(12) United States Patent
Chen et al.

(10) Patent No.: US 8,546,366 B2
(45) Date of Patent: Oct. 1, 2013

(54) METHOD FOR INHIBITION OF TUMOR CELL GROWTH USING (22R)-5α-LANOSTA-8,24-DIEN-3β,15α,21-TRIOL

(75) Inventors: Yu-Jen Chen, Taipei (TW); Cheng-Jen Chou, Taipei (TW); Tun-Tschu Chang, Taipei (TW)

(73) Assignee: Mackay Memorial Hospital, Taipei (TW)

( * ) Notice: Subject to any disclaimer, the term of this patent is extended or adjusted under 35 U.S.C. 154(b) by 34 days.

(21) Appl. No.: 13/483,620

(22) Filed: May 30, 2012

(65) Prior Publication Data
US 2012/0309732 A1 Dec. 6, 2012

(30) Foreign Application Priority Data

May 31, 2011 (TW) .............................. 100119159 A

(51) Int. Cl.
*A61K 31/56* (2006.01)
*A61K 38/00* (2006.01)
*A61P 35/00* (2006.01)

(52) U.S. Cl.
USPC ............................................ 514/182; 514/19.3

(58) Field of Classification Search
None
See application file for complete search history.

(56) References Cited

PUBLICATIONS

Shen et al. New lanostanes and naphthoquinones isolated from Antrodia salmonea and their antioxidative burst activity in human leukocytes. Planta Medica. 2006; 72: 199-203.*
Yeh et al. Cytotoxic triterpenes from Antrodia camphorata and their mode of action in HT-29 human colon cancer cells. Cancer Letters, 2009, 73-79.*

* cited by examiner

*Primary Examiner* — Anna Pagonakis
(74) *Attorney, Agent, or Firm* — WPAT, P.C.; Anthony King

(57) ABSTRACT

In this patent, we isolated a novel compound from fruiting body of *Antrodia cinnamomea*, namely, (22R)-5α-lanosta-8,24-dien-3β,15α,21-triol. This compound possesses preferential cytotoxicity against human leukemia, pancreatic cancer, esophageal cancer, hepatoma, and cervical cancer cells.

4 Claims, 4 Drawing Sheets

A. human leukemia U937 cells - control

B. human leukemia U937 cells - 10 µg/mL

A.

B.

A. human normal monocyte - control

B. human normal monocyte - 5 µg/mL

METHOD FOR INHIBITION OF TUMOR CELL GROWTH USING (22R)-5α-LANOSTA-8,24-DIEN-3β,15α,21-TRIOL

BACKGROUND OF THE INVENTION

1. Field of the Invention

The present invention is related to a method for inhibition of a tumor cell growth, especially relating to a method for inhibition of a tumor cell growth by using the compound which is (22R)-5α-lanosta-8,24-dien-3β,15α,21-triol.

2. The Prior Arts

*Antrodia cinnamomea*, a Taiwan endemic species of fungi which also known as Niu Chang-Zhi or Chang-Ku, is a perennial mushroom belonging to the family Polyporaceae and genus of *Antrodia*. *Antrodia cinnamomea* grows on the inner rotten wall of the hollow material from Taiwan's Lauraceae tree species, *Cinnamomum kanehirai*. The composition of *Antrodia cinnamomea* is multiple, complex and containing plenty bioactive compounds, such as polysaccharides, triterpenoids, small molecular proteins, vitamins, minerals, nucleotides, steroids, and blood pressure stabilizing agents. In Taiwan's folk medicine, *Antrodia cinnamomea* is recognized as great antidote for detoxifying food poisoning and pesticide poisoning.

Leukemia, commonly called blood cancer, is a type of hematological cancer that has highest incidence rate among all children cancers. Although the treatment of leukemia has evolved greatly, recurrence of leukemia is still high and there is no cure for this cancer. Pancreatic cancer commonly is a type of pancreatic duct adenocarcinoma originated from the epithelium of human pancreatic ducts. Because the pancreatic duct is hidden behind the organs and located at the back of abdomen, therefore, early detection of pancreatic cancer is difficult. Furthermore, pancreatic cancer is resistant to standard chemotherapy and radiotherapy, resulting to its characteristics of spreading rapidly and aggressively into surrounding tissues and high relapse rate. Treatments of adult pancreatic cancer, hepatoma, and esophageal cancer are still not perfect when these cancers can not be surgically excised. Five-year survival rate of these cancers is lower than 5%. Cervical adenocarcinoma is a type of cervical cancers that has high risk to relapse and spread, and the cancer is relatively resistant to the standard treatment.

For cancer treatment with cytotoxic agents, the major dose-limiting factor is their toxicity to normal cells and tissues. This safety consideration is particularly critical in the late stage and terminal stage cancer patients, as they are known as a less-tolerant population. Therefore, development of novel compounds with less toxicity to normal cells but with high destructive activity towards tumor cells are urgent.

Although currently extracts of *Antrodia cinnamomea* have been reported to have therapeutic effects, bioactive components in *Antrodia cinnamomea* extracts that contributing to the inhibition of tumor cell growth are still in early development stage. In addition, few scientific studies provide detailed information of the bioactive compounds which require in depth studies. Therefore, it will be great contribution and beneficial effect to cancer patients if active compounds in *Antrodia cinnamomea* extract are further purified and identified and subsequently applied in inhibition of hepatoma, hepatoma, esophageal cancer, cervical adenocarcinoma, pancreatic cancer and leukemia.

SUMMARY OF THE INVENTION

In order to identify the anti-cancer compounds from the extracts of *Antrodia cinnamomea*, a compound was isolated and purified in the present invention, and the compound is designated as (22R)-5α-lanosta-8,24-dien-3β,15α,21-triol, with chemical formula as $C_{30}H_{50}O_3$ and molecular weight of 458.3756.

(22R)-5α-lanosta-8,24-dien-3β,15α,21-triol of the present invention is isolated and purified from extracts of *Antrodia cinnamomea* fruiting bodies extracted with organic solvents. The organic solvents used include, but not limited to, alcohols (for example, methanol, ethanol, or propanol), esters (for example, ethylacetate), alkenes (for example, hexane) or haloagenated alkens (for example, chloromethane, chloroethane); wherein, ethanol is preferred. Any solvent that can extract the compound of the present invention can be used in this method.

The compound of the present invention can inhibit tumor cell growth through induction of apoptosis of human solid tumor, such as hepatoma, esophageal cancer, cervical adenocarcinoma and pancreatic cancer. In addition, the mechanism of the compound of the present invention to inhibit growth of blood cancer growth such as human leukemic cell U937 is through apoptosis and mitotic catastrophe pathway.

The present invention is related to the method of the compound abovementioned used on inhibition of tumor cell growth, which can be further used as a pharmaceutical composition for cancer treatment to enhance therapeutic effects. Scope of the present invention's method includes inhibition in tumor cell growth of leukemia, hepatoma, esophageal cancer, cervical adenocarcinoma, or pancreatic cancer. In treatment of these cancers, which subsequently leading to reduced tumor cell growth rate, inhibition of tumor cell proliferation, and delayed deterioration of cancer. Thus, the compound of the present invention can be applied in treatment of hepatoma, esophageal cancer, cervical adenocarcinoma, pancreatic cancer or leukemia.

On the other hand, the compound of the present invention can be incorporated into pharmaceutical compositions for treating leukemia and solid tumors to inhibit the tumor cell growth. The pharmaceutical compositions include not only the compound in an effective amount, but also the pharmaceutically acceptable carriers. Examples of such carriers include, but are not limited to, excipients such as water, fillers such as sucrose or starch, binders such as cellulose derivatives, diluents, disintegrants, absorption enhancers or sweeteners. The pharmaceutical composition of the present invention can be manufactured through mixing the compound in an effective amount with at least one of the carriers by means of conventional methods known in the pharmaceutically technical field, which can be formulated in the form of, but are not limited to, powder, tablets, capsules, pellets, granules or other liquid formulation.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Figure 1:
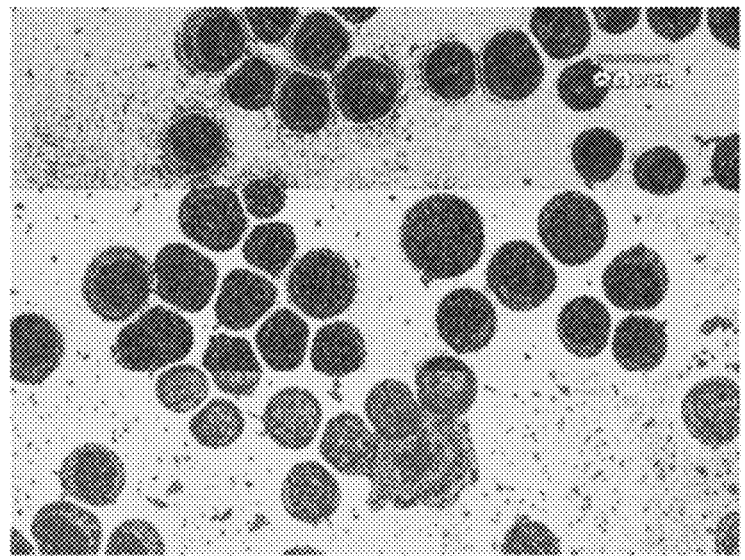
FIG. 1 is a morphological assessment of human leukemic U937 cells treated by the compound. Liu's stain method was used for morphological observation. (A) Control group and (B) Experimental group (treated with 10 μg/ml of the compound for 3 days).
Figure 1:
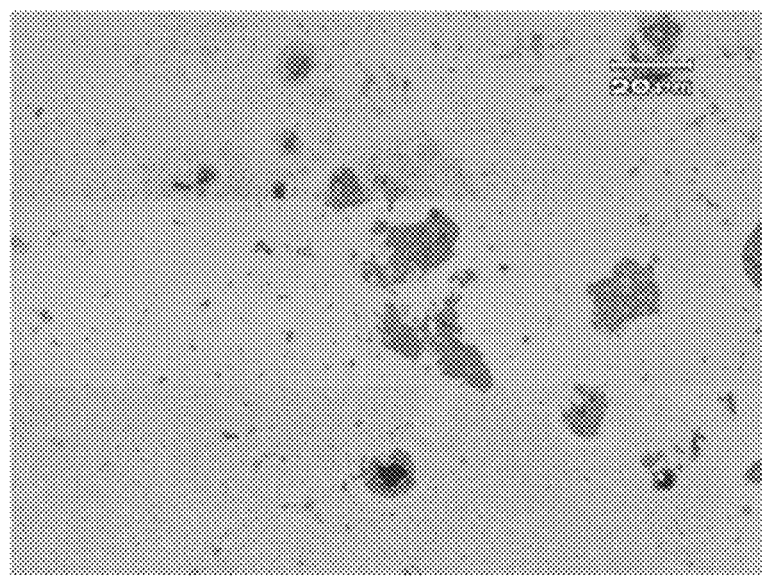

Fruiting body of *Antrodia cinnamomea* was extracted with the techniques known in the prior arts, such as extraction with water or organic solvents to collect water extracts or solvent extracts. The organic solvents used include, but not limited to, alcohols (for example, methanol, ethanol, or propanol), esters (for example, ethylacetate), alkenes (for example, hexane) or haloagenated alkens (for example, chloromethane, chloroethane); wherein alcohols is preferred, and ethanol is most preferred. A crude extract of *Antrodia cinnamomea* was further purified by column chromatography, and anti-cancer activity of each compound purified from the extract was evaluated. Compounds of eluted fractions with anti-tumor activity were further analyzed by nuclear magnetic resonance (NMR), Mass Spectrometry (MS)/UV, or enantiomeric excess to determine its configuration. The compound was elucidated as (22R)-5α-lanosta-8,24-dien-3β,15α,21-triol, with molecular formula of $C_{30}H_{50}O_3$ and molecular weight of 458.3756. The compound can selectively inhibit tumor cells but show no effect on normal human peripheral blood monocytes.

To demonstrate inhibitory effect of the compound on tumor cell growth, the present invention used MTT (3-(4,5-dimethylthiazol-2-yl)-2,5-diphenyl-tetrazolium bromide, MTT) method to evaluate its anti-cancer activity, according to the anti-cancer drug screening model of National Cancer Institute (NCI) on survival rates using cell lines of hepatoma, esophageal cancer, cervical adenocarcinoma, pancreatic cancer or ovarian cancer. Inhibitory mechanism of the compound on tumor cell growth was elucidated through observation of the cell morphology and cell cycle change after the treatment with the compound. These test results proved that the compound significantly inhibited human leukemia cells U937, pancreatic cells BxPC-3, esophageal tumor cells CE-81T/VGH, hepatoma cells HA22T/VGH and cervical adenocarcinoma cells HeLa, except ovarian tumor cells SKOV-3. The inhibition rate of the compound on these tumor cell lines was in the range of 48.5~99.8%. These tests are further described in the following Examples.

EXAMPLE 1

Purification of the (22R)-5α-lanosta-8,24-dien-3β, 15α,21-triol

One thousand and twelve grams of Fruiting bodies of *Antrodia cinnamomea* were extracted four times with distilled water (4×10 L) at 85° C. with techniques known in the field. The residues of fruiting bodies were then heated and extracted five times with ethanol reflux 5 times (5×20 L) for 6 hours, followed by evaporation of ethanol. Crude ethanol extract concentrate (354.2 g) was re-suspended in 2 L of distilled water, and partitioned between dichloromethane and water (volume ratio 1:1) to afford organic and aqueous fractions. The organic solvent layer was evaporated to remove organic solvent and residues collected (311.5 g) was dissolved in 1.5 L of methanol to get methanol dissolvable portion (294.6 g) and methanol indissolvable portion (15.1 g). The methanol dissolvable portion was first subjected to silica gel column chromatography using n-hexane/ethyl acetate gradient as the mobile phase, and followed by a second dichloromethand/methanol gradient elution for further isolation and purification. 500 ml of each fraction eluent solvent was collected and subjected to Thin toluene Chromatography (TLC) using a silica gel adsorbent and a benzene/ethyl acetate/acetic acid (10:1:0.5) developing solvent system was then used to isolate 10 fractions (Fr I~X). Fraction IV (53.1 g) was again treated with methanol to obtain methanol dissolvable portion and methanol insoluble portion. The methanol dissolvable portion (Fr IV-MS, 51.6 g) was subjected to silica gel MPLC chromatography using hexane/acetone as mobile gradient as mobile phase, thus yielding 38 sub-fractions (Fr IV-MS-1~38). Fr IV-MS-26 was again first subjected to silica gel chromatography using hexane/acetone gradient as mobile phase and followed by a second column chromatography (HPLC, using Cosmosil $5C_{18}$-AR-II column (20×250 mm) and 70~100% methanol (containing 0.5% acetic acid) as gradient elution system with flow rate at 16 ml/min; UV detection wavelength set at 210 nm). Finally 12 mg of the compound was obtained.

The compound which was a white powder was designated as (22R)-5α-lanosta-8,24-diene-3β,15α,21-triol, with molecular formula of $C_{30}H_{50}O_3$ and molecular weight of 458.3756. The melting point of the compound was 168~170° C.; $[\alpha]_D^{25}$:+41.9° (methanol, c 0.62). The results of NMR analysis were shown in Table 1.

TABLE 1

Spectra Data of $^1$H-NMR(500 MHz) and $^{13}$C-NMR(125 MHz)(Pyridine-$d_5$) of the Compound which is (22R)-5α-lanosta-8,24-dien-3β,15α,21-triol

| position | $\delta_C$ | $\delta_H$ |
|---|---|---|
| 1 | 36.2 t | 1.26 m, 1.72 m |
| 2 | 28.8 t | 1.88 |
| 3 | 78.1 d | 3.46 t(8.0) |
| 4 | 39.5 s | |
| 5 | 50.9 d | 1.24 m |
| 6 | 18.9 t | 1.60 m, 1.82 m |
| 7 | 27.8 t | 2.56 m, 2.76 m |
| 8 | 135.1 s | |
| 9 | 135.2 s | |
| 10 | 37.5 s | |
| 11 | 21.3 t | 2.04 m, 2.16 m |
| 12 | 31.7 t | 1.86 m, 2.14 m |
| 13 | 45.3 s | |
| 14 | 52.4 s | |
| 15 | 72.6 d | 4.60 t(7.0) |
| 16 | 39.9 t | 2.22 m |
| 17 | 43.8 d | 2.40 m |
| 18 | 16.9 q | 0.98 s |
| 19 | 19.4 q | 1.08 s |
| 20 | 44.1 d | 1.74 m |
| 21 | 62.0 t | 3.92 dd(9.0, 5.0), 4.08 d (9.0) |
| 22 | 30.7 t | 1.79 m |
| 23 | 25.5 t | 2.18 m, 2.34 m |
| 24 | 126.1 d | 5.27 t(7.0) |
| 25 | 130.8 s | |
| 26 | 25.8 q | 1.65 s |
| 27 | 17.7 q | 1.58 s |
| 28 | 18.2 q | 1.34 s |
| 29 | 28.5 q | 1.22 s |
| 30 | 16.4 q | 1.07 s |

EXAMPLE 2

In Vitro Anti-leukemic Cell Activity Assay

Examples of the present invention adopted anti-tumor drugs screening model of National Cancer Institute (NCI) to examine inhibitory effect of the compound on cancer cells. The compound was added into culture medium containing leukemic cells U937 (a human monoblastoid leukemic cell line) to test for tumor cell survival. Cell survival rate is determined by well known MTT assay, and U937, a human myeloid leukemic cell line obtained from American Type Culture Collection (ATCC), is belonged to one of human acute leukemic cell lines and is classified as monoblasts during hematopoietic differentiation.

MTT assay is a commonly used method for analysis of percent of viable cells, wherein MTT (3-[4,5-dimethylthiazol-2-yl]2,5-diphenyltetrazolium bromide) is a yellow color dye that can be absorbed by living cells and be converted by mitochondria succinate tetrazolium reductase to water insoluble purple-blue formazan. Therefore, the amount of formazan formation can be used as an assessment tool to determine the survival rate of cells.

The human leukemia cell line U937 was cultivated in RPMI 1640 medium containing fetal calf serum for 24 hours and maintained in the exponential growth condition. The proliferating cells were treated with the compound in the concentration of 0 (the control group), 1.25, 2.5, 5 or 10 μg/ml at 37° C. under 5% $CO_2$ for 24-72 hours, respectively. Then MTT was added in a concentration of 500 μg/ml into each wells in the dark and incubated for 4 hours, followed by the addition of 500 μl of isopropanol to stop the reaction. The plates were read on an ELISA reader at wavelength of 570 nm to determine the cell survival rates. The results were reported as the average±(plus/minus) SEM (Standard Error in the Mean). For statistical analysis, the t-test was used to compare the difference between each experiment result. $p<0.05$ was considered statistically significant.

The results indicated that the compound, in the concentration of 1.25、2.5、5、10 μg/ml, could inhibit the growth of human leukemic cell U937 effectively at the first day of the experiment. Positive correlations were established between the inhibition ability and the concentration of the compound. The inhibitory rates were all increased to a rate of more than 60% at the third day of the experiment, and the inhibitory rates in the concentration of 5 and 10 μg/ml groups increased to a rate of more than 95%, and up to a highest rate of 99.8%. The $IC_{50}$ value of the compound toward U937 cells was about 2 μg/ml. These results showed inhibitory effects of the compound from *Antrodia cinnamomea* in leukemic cells, and the inhibitory effects were in a dose- and time-dependent manner.

EXAMPLE 3

In Vitro Anti-Cancer Activity Against Pancreatic Cancer Cells

The test adopted the cell survival analysis (i.e., the MTT assay as described above). The purified compound was added into the culture media with human pancreatic cancer cell line BxPC-3 to test for tumor cell survival. This survival assay was carried out with the abovementioned MTT assay, wherein the pancreatic cancer cell line BxPc-3 was purchased from American Type Culture Collection (ATCC), the cell line originated from the epithelium of human pancreatic adenocarcinomas.

The human pancreatic cancer cell line BxPc-3 was cultivated in DMEM media containing 100 IU/ml penicillin (Invitrogen, Carlsbad, Calif.), 100 μg/ml streptomycin (Invitrogen, Carlsbad, Calif.), 2 mM glutamin (Invitrogen, Carlsbad, Calif.), and 10% fetal calf serum (Atlanta Biologicals, Norcross, Ga.). The proliferated cells were treated with the compound in the concentration of 0 (the control group), 5 and 10 μg/ml (the experimental group), respectively. The cells were incubated at 37° C. in a 5% $CO_2$ incubator for 24-72 hours. 500 μg/ml of MTT was added into each well in the dark and incubated for 4 hours, followed by the addition of 500 μl of isopropanol to stop the reaction. The plates were read on an ELISA reader at wavelength of 570 nm to determine the cell survival rates. The results were reported as the average±(plus/minus) SEM (Standard Error in the Mean). For statistical analysis, the t-test was used to compare the difference between each experiment result. $p<0.05$ was considered statistically significant.

The results indicated that the compound could significantly inhibit the growth of pancreatic cancer cell line BxPc-3, and positive correlations were established between the inhibition ability and the concentration of the compound or incubation time. The inhibitory rates were all increased at the third day of experiment in the concentration of 5 and 10 μg/ml groups, which up to a highest rate of 48.5%. These results showed inhibitory effects of the compound from *Antrodia cinnamomea* in human pancreatic cancer cells, and the inhibitory effects were in a dose- and time-dependent manner.

EXAMPLE 4

In Vitro Anti-Tumor Activity Against Esophageal Cancer

The purified compound was added into the culture media with human esophageal cancer cell line CE-81T/VGH to test for tumor cell survival. This survival assay was carried out with the abovementioned MTT assay, wherein the CE-81T/VGH esophageal cancer cell line was obtained from Taipei Veteran General Hospital, the cell line originated from the epithelium of human esophageal cancer cells.

The human esophageal cancer cell line CE-81T/VGH was cultivated in DMEM media containing 100 IU/ml penicillin (Invitrogen, Carlsbad, Calif.), 100 μg/ml streptomycin (Invitrogen, Carlsbad, Calif.), 2 mM glutamin (Invitrogen, Carlsbad, Calif.), and 10% fetal calf serum (Atlanta Biologicals, Norcross, Ga.). The proliferated cells were treated with the compound in the concentration of 0 (the control group) and 5 μg/ml (the experimental group), respectively. The cells were incubated at 37° C. in a 5% $CO_2$ incubator for 24-72 hours. 500 μg/ml of MTT was added into each well in the dark and incubated for 4 hours, followed by the addition of 500 μl of isopropanol to stop the reaction. The plates were read on an ELISA reader at wavelength of 570 nm to determine the survival rates.

The results indicated that the compound could inhibit the growth of human esophageal cancer cells CE-81T/VGH. The inhibitory rate in the concentration of 5 μg/ml group was 61.4% after 72 hours of treatment.

EXAMPLE 5

In Vitro Anti-Tumor Activity Against Hepatoma Cells

The test adopted the cell survival analysis (i.e., the MTT assay as described above). The purified compound was added into the culture media with human hepatoma cell line HA22T/VGH to test for tumor cell survival. This survival assay was carried out with the abovementioned MTT assay, wherein the hepatoma cell line HA22T/VGH was obtained from Taipei Veteran General Hospital, the cell line originated from the human hepatoma.

The human hepatoma cell line HA22T/VGH was cultivated in DMEM media containing 100 IU/ml penicillin (Invitrogen, Carlsbad, Calif.), 100 µg/ml streptomycin (Invitrogen, Carlsbad, Calif.), 2 mM glutamin (Invitrogen, Carlsbad, Calif.), and 10% fetal calf serum (Atlanta Biologicals, Norcross, Ga.). The proliferated cells were treated with the compound in the concentration of 0 (the control group) and 5 µg/ml (the experimental group), respectively. The cells were incubated at 37° C. in a 5% $CO_2$ incubator for 24-72 hours. 500 µg/ml of MTT was added into each well in the dark and incubated for 4 hours, followed by the addition of 500 µl of isopropanol to stop the reaction. The plates were read on an ELISA reader at wavelength of 570 nm to determine the survival rates.

The results indicated that the compound could inhibit the growth of human hepatoma cells HA22T/VGH. The inhibitory rate in the concentration of 5 µg/ml group was 90.3% after 72 hours of treatment.

EXAMPLE 6

In Vitro Anti-Tumor Activity Against Cervical Adenocarcinoma Cells

The test adopted the cell survival analysis (i.e., the MTT assay as described above). The purified compound was added into the culture media with human cervical adenocarcinoma cell line HeLa to test for tumor cell survival. This survival assay was carried out with the abovementioned MTT assay, wherein the cervical adenocarcinoma cell line HeLa was purchased from American Type Culture Collection (ATCC), the cell line originated from the epithelium of human cervical adenocarcinoma.

The human cervical adenocarcinoma cell line HeLa was cultivated in DMEM media containing 100 IU/ml penicillin (Invitrogen, Carlsbad, Calif.), 100 µg/ml streptomycin (Invitrogen, Carlsbad, Calif.), 2 mM glutamin (Invitrogen, Carlsbad, Calif.), and 10% fetal calf serum (Atlanta Biologicals, Norcross, Ga.). The proliferated cells were treated with the compound in the concentration of 0 (the control group) and 5 µg/ml (the experimental group), respectively. The cells were incubated at 37° C. in a 5% $CO_2$ incubator for 24-72 hours. 500 µg/ml of MTT was added into each well in the dark and incubated for 4 hours, followed by the addition of 500 µl of isopropanol to stop the reaction. The plates were read on an ELISA reader at wavelength of 570 nm to determine the survival rates.

The results indicated that the compound could inhibit the growth of human cervical adenocarcinoma cells HeLa. The inhibitory rate in the concentration of 5 µg/ml group was 56.8% after 72 hours of treatment.

EXAMPLE 7

In Vitro Anti-Tumor Activity Against Ovarian Cancer Cells

The test adopted the cell survival analysis (i.e. the MTT assay as described above). The purified compound was added into the culture media of human ovarian cancer cell line SKOV-3 to test for tumor cell survival. This survival assay was carried out with the abovementioned MTT assay, wherein the ovarian cancer cell line SKOV-3 was purchased from American Type Culture Collection (ATCC), the cell line originated from the epithelium of human ovarian cancer.

The human ovarian cancer cell line SKOV-3 was cultivated in DMEM media containing 100 IU/ml penicillin (Invitrogen, Carlsbad, Calif.), 100 µg/ml streptomycin (Invitrogen, Carlsbad, Calif.), 2 mM glutamin (Invitrogen, Carlsbad, Calif.), and 10% fetal calf serum (Atlanta Biologicals, Norcross, Ga.). The proliferated cells were treated with the compound in the concentration of 0 (the control group) and 5 µg/ml (the experimental group), respectively. The cells were incubated at 37° C. in a 5% $CO_2$ incubator for 24-72 hours. 500 µg/ml of MTT was added into each well in the dark and incubated for 4 hours, followed by the addition of 500 µl of isopropanol to stop the reaction. The plates were read on an ELISA reader at wavelength of 570 nm to determine the survival rates.

The results indicated that the compound could not inhibit the growth of human ovarian cancer cells SKOV-3 after 72 hours of treatment.

EXAMPLE 8

Cell Cycle Analysis on Cancer Cells After the Treatment of the (22R)-5α-lanosta-8,24-dien-3β,15α,21-triol Flow cytometer was used to analyze the effect of the compound on cell cycle of human leukemic cells.

The compound in concentration of 10 µg/ml was used to treat human leukemic cell line U937, and cells without addition of compound were served as the control group. The treated cells after 72 hours of treatment were stained with Liu's stain method for morphological observation, as shown in FIG. 1.

The compound in concentration of 2.5 µg/ml was used to treat human leukemic cell line U937, and cells without addition of compound were served as the control group. The treated cells after 48 hours of treatment were fixed at 4° C. with 70% ethanol for 1 hour and stained for 30 minutes with propidium iodide solution (0.5 mg/ml of propidium iodide; 0.1 mg/ml of RNAse) contained in a CycleTEST PLUS DNA reagent kit (Becton Dickinson, Lincoln Park, N.J.). DNA content measurement on the collected $10^4$ cells was performed on the FACS Calibur flow cytometer (Becton Dickinson), and the cell cycle changes were analyzed using a ModFit software (Becton Dickinson). Results were shown in FIG. 2.

Figure 2:
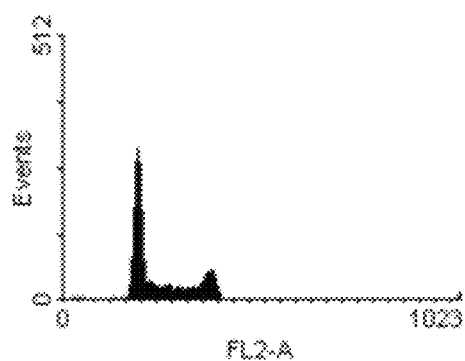
FIG. 2 is a cell cycle analysis of human leukemic U937 cells treated by the compound. DNA histograms are demonstrated. (A) Control group and (B) Experimental group (treated with 2.5 μg/ml of the compound for 2 days).
Figure 2:
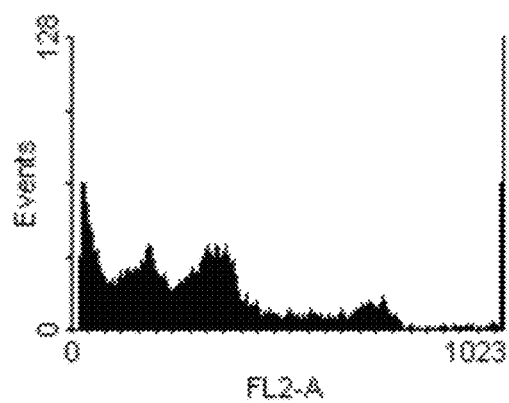

Referring to the FIG. 2, the result showed that leukemic cells U937 exhibited special cell cycle distribution, including hypoploidy, G2/M phase arrest, and polyploidy. This result showed that the compound would induce apoptosis and mitotic catastrophe.

EXAMPLE 9

Effect of the (22R)-5α-lanosta-8,24-dien-3β,15α,21-triol on Inter-Nucleosomal DNA Cleavage of Tumor Cells In addition to the morphological changes described above, cells may show some biochemical changes during cell apoptosis, including chromatin condensation, formation of apoptotic body due to cell fragmentation, and inter-nucleosomal cleavage of DNA that leading to formation of DNA ladder in DNA electrophoresis. To confirm the relationship of inhibition activity between the compound and the stage of cell apoptosis, the experiment adopted DNA electrophoresis to examine inter-nucleosomal cleavage of DNA into DNA ladder at late stage of cell apoptosis.

Figure 3:
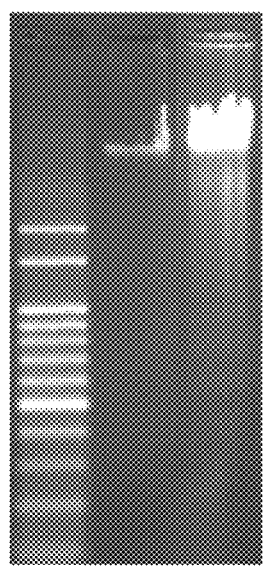
FIG. 3 shows a DNA gel electrophoresis. Lane 1, molecular marker; Lane 2, control group; Lane 3, experimental group (treated with 5 μg/ml of the compound for 24 hours).

The results of DNA electrophoresis demonstrated that the compound induced the genomic DNA into oligonucleosomal fragmentations, a hallmark of apoptosis. Total DNAs were extracted and analyzed by 1.5% agarose gel electrophoresis in TBE buffer (5 mM TBE buffer containing 1 μM EDTA, pH 8.0). The gel was stained with ethidium bromide and visualized under UV. The results were shown in FIG. 3.

EXAMPLE 10

Effect of the (22R)-5α-lanosta-8,24-dien-3β,15α,21-triol on Mitochondria Transmembrane Potential and Caspase of Cancer Cells Human leukemic cell U937 was treated with the compound (5 μg/ml) for 16 hours. The same cells treated with anti-tumor agent camptothecin (4 μM) for 16 hours were used as positive control group, while untreated cells were used as control group. The cells were then washed with PBS solution, followed by addition of 40 nM 3,3'-dihexyloxacarbocyanine (DiOC6(3); Molecular Probes, Eugene, Oreg.) into culture medium at 37° C. in the dark and incubated for 15 minutes. The results were analyzed immediately using flow cytometry, wherein the excitation wavelength was set at 488 nm and emission wavelength set at 530 nm to detect fluorescence density and as representative of mitochondria transmembrane potential change.

In the process of cell apoptosis mitochondria transmambrane potential dropped when mitochondria pathway was affected. Human leukemic cells U937 treated with the compound did not be exhibited significantly reduction of transmembrane potential, suggesting the compound induced mitochondria-independent pathway.

Therefore, the compound did not change the mitochondrial transmembrane potential, indicating a mitochondria-independent pathway. Caspase 3 and pan-caspase inhibitors could block the camptothecin-induced growth inhibition but not that induced by the compound. Furthermore, the expression of caspase 3 and caspase 8 was not altered by adding the compound. Thus, the compound may induce apoptosis in a caspase-independent pathway.

EXAMPLE 11

Figure 4:
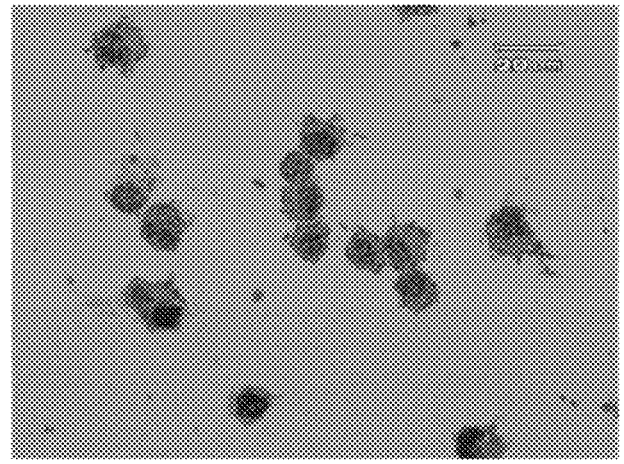
FIG. 4 is a morphological assessment of human normal peripheral blood monocytes treated by the compound. Liu's stain method was used for morphological observation. (A) Control group and (B) Experimental group (treated with 5 μg/ml of the compound for 1 day).
Figure 4:
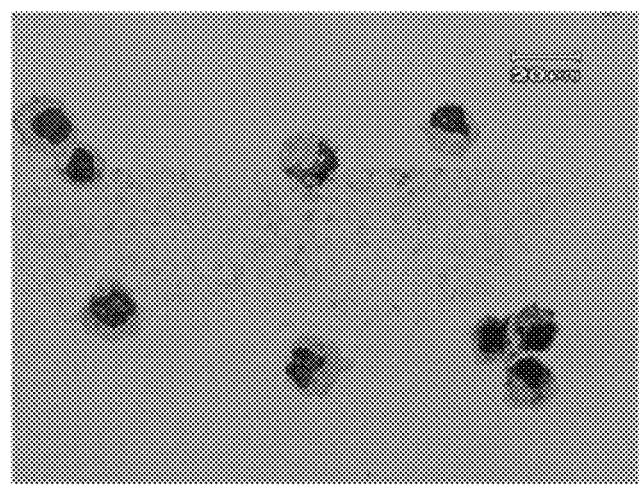

Effect of the (22R)-5α-lanosta-8,24-dien-3β,15α,21-triol on Human Normal Monocytes The compound showed only slightly viability inhibition (<10%) in human normal monocytes isolated from peripheral blood mononuclelar cells. The results were shown in FIG. 4.

From the example described above, it is known that the compound can inhibit growth of human leukemic cells U937 up to 99.8%. At low concentration (5 μg/ml), the inhibition rate of the compound on human hepatoma cell HA22T/VGH, pancreatic cancer cell BxPc-3, esophageal cancer cell CE-81T/VGH, and cervical adenocarcinoma cell HeLa is 90.3%, 49.1%, 61.4% and 56.8%, respectively.

From the examples described above, the compound exhibited preferential cytotoxic activity against human leukemic cells, pancreatic cells, esophageal cancer cells, hepatoma and cervical adenocarcinoma cell without toxicity to normal monocytes.

On the other hand, the compound of the present invention can be incorporated into pharmaceutical compositions for treating the leukemia, pancreatic cancer, hepatoma, esophageal cancer, and cervical adenocarcinoma to inhibit the growth of tumor cells. The pharmaceutical compositions included not only the compound in an effective amount, but also pharmaceutically acceptable carriers. Examples of such carriers include, but are not limited to, excipients such as water, fillers such as sucrose or starch, binders such as cellulose derivatives, diluents, disintegrants, absorption enhancers or sweeteners. The pharmaceutical composition according to the present invention can be manufactured through mixing the compound in an effective amount with at least one of the carriers by means of conventional methods known in the pharmaceutically technical field, which can be formulated, but are not limited to, as a powder, tablet, capsule, pellets, granules or other liquid formulation.

What is claimed is:

1. A method for inhibition of esophageal cancer cell growth, comprising administering an effective amount of a compound which is (22R)-5α-lanosta-8,24-dien-3β,15α,21-triol.

2. The method as claimed in claim 1, wherein the compound induces cell apoptosis.

3. The method as claimed in claim 2, wherein the compound induces cell apoptosis by increasing the ratio of sub-G1 nucleus population in the esophageal cancer cells.

4. The method as claimed in claim 3, wherein the esophageal cancer cell is CE-81T/VGH cell line.

* * * * *